(12) United States Patent
Johns

(10) Patent No.: US 7,791,491 B2
(45) Date of Patent: Sep. 7, 2010

(54) MEASURING ALERTNESS

(75) Inventor: Murray Johns, Richmond (AU)

(73) Assignee: Sleep Diagnostics Pty., Ltd, Victoria (AU)

( * ) Notice: Subject to any disclaimer, the term of this patent is extended or adjusted under 35 U.S.C. 154(b) by 308 days.

(21) Appl. No.: 11/817,608

(22) PCT Filed: Mar. 6, 2006

(86) PCT No.: PCT/AU2006/000277

§ 371 (c)(1),
(2), (4) Date: Aug. 31, 2007

(87) PCT Pub. No.: WO2006/092022

PCT Pub. Date: Sep. 8, 2006

(65) Prior Publication Data

US 2008/0150734 A1   Jun. 26, 2008

(30) Foreign Application Priority Data

Mar. 4, 2005   (AU) .............................. 2005901026

(51) Int. Cl.
*G08B 23/00* (2006.01)
(52) U.S. Cl. .................. 340/576; 340/575; 600/558
(58) Field of Classification Search .................. 340/575
See application file for complete search history.

(56) References Cited

U.S. PATENT DOCUMENTS

| 4,359,724 | A |  | 11/1982 | Zimmerman et al. |
| 4,838,681 | A |  | 6/1989 | Pavlidis |
| 5,311,877 | A | * | 5/1994 | Kishi .......................... 600/545 |
| 5,570,698 | A | * | 11/1996 | Liang et al. .................. 600/558 |
| 5,786,765 | A | * | 7/1998 | Kumakura et al. ........... 340/576 |
| 5,795,306 | A | * | 8/1998 | Shimotani et al. ........... 600/558 |
| 6,082,858 | A |  | 7/2000 | Grace et al. |
| 6,163,281 | A |  | 12/2000 | Torch |
| 6,304,187 | B1 | * | 10/2001 | Pirim .......................... 340/576 |

(Continued)

FOREIGN PATENT DOCUMENTS

AU   8788801   4/2002

(Continued)

OTHER PUBLICATIONS

Ji et al., "Real-Time Eye, Gaze, and Face Pose Tracking for Monitoring Driver Vigilance", Real Time Imaging (8); pp. 357-377 (2002).

(Continued)

*Primary Examiner*—Benjamin C Lee
*Assistant Examiner*—Curtis J King
(74) *Attorney, Agent, or Firm*—Connolly Bove Lodge & Hutz LLP

(57) ABSTRACT

A method and apparatus for measuring drowsiness particularly in vehicle operators measures the amplitude to velocity ratio for eyelids closing and opening during blinking as well as measuring duration of opening and closing. The average values for the amplitude to velocity ratios for opening and closing are weighted and added to give a drowsiness measure that is compared to a scale of drowsiness based on data collected from alert and drowsy subjects. Other eye movements can be used in the weighted algorithm. The scale of drowsiness predicts the onset of drowsiness levels that render an operator unfit to continue.

6 Claims, 8 Drawing Sheets

Blink in a drowsy subject
amp = amplitude of blink
mev = maximum closing velocity of eyelid
mov = maximum reopening velocity of eyelid
inter-event time = a measure of blink duration
velocity = change in position per 50 msec

U.S. PATENT DOCUMENTS

| | | | |
|---|---|---|---|
| 6,346,887 | B1 | 2/2002 | Van Orden et al. |
| 7,301,465 | B2 * | 11/2007 | Tengshe et al. .............. 340/575 |
| 7,344,251 | B2 * | 3/2008 | Marshall ...................... 351/246 |
| 2004/0233061 | A1 * | 11/2004 | Johns .......................... 340/575 |
| 2006/0083409 | A1 * | 4/2006 | Yuzawa et al. ............... 382/116 |
| 2006/0103539 | A1 * | 5/2006 | Isaji et al. .................... 340/575 |

FOREIGN PATENT DOCUMENTS

| | | |
|---|---|---|
| FR | 2784887 | 4/2000 |
| JP | 06266981 | 9/1994 |
| JP | 2001005952 | 1/2001 |

OTHER PUBLICATIONS

Grace et al., "A Drowsy Driver Detection System for Heavy Vehicles", IEEE, (1998).

Perclos: "A Valid Psychophysiological Measure of Alertness As Assessed by Psychomotor Vigilance", Federal Highway Administraton, Office of Motor Carrier Research & Standards (1998).

Bagci et al., "Eye Tracking Using Markov Models", IEEE Proceedings of the 17th International Conference on Pattern Recognition (ICPR 2004).

Hartley et al., "Review of Fatigue Detection & Prediction Technologies", National Road Transport Commission, pp. 1-31, Sep. 2000.

* cited by examiner

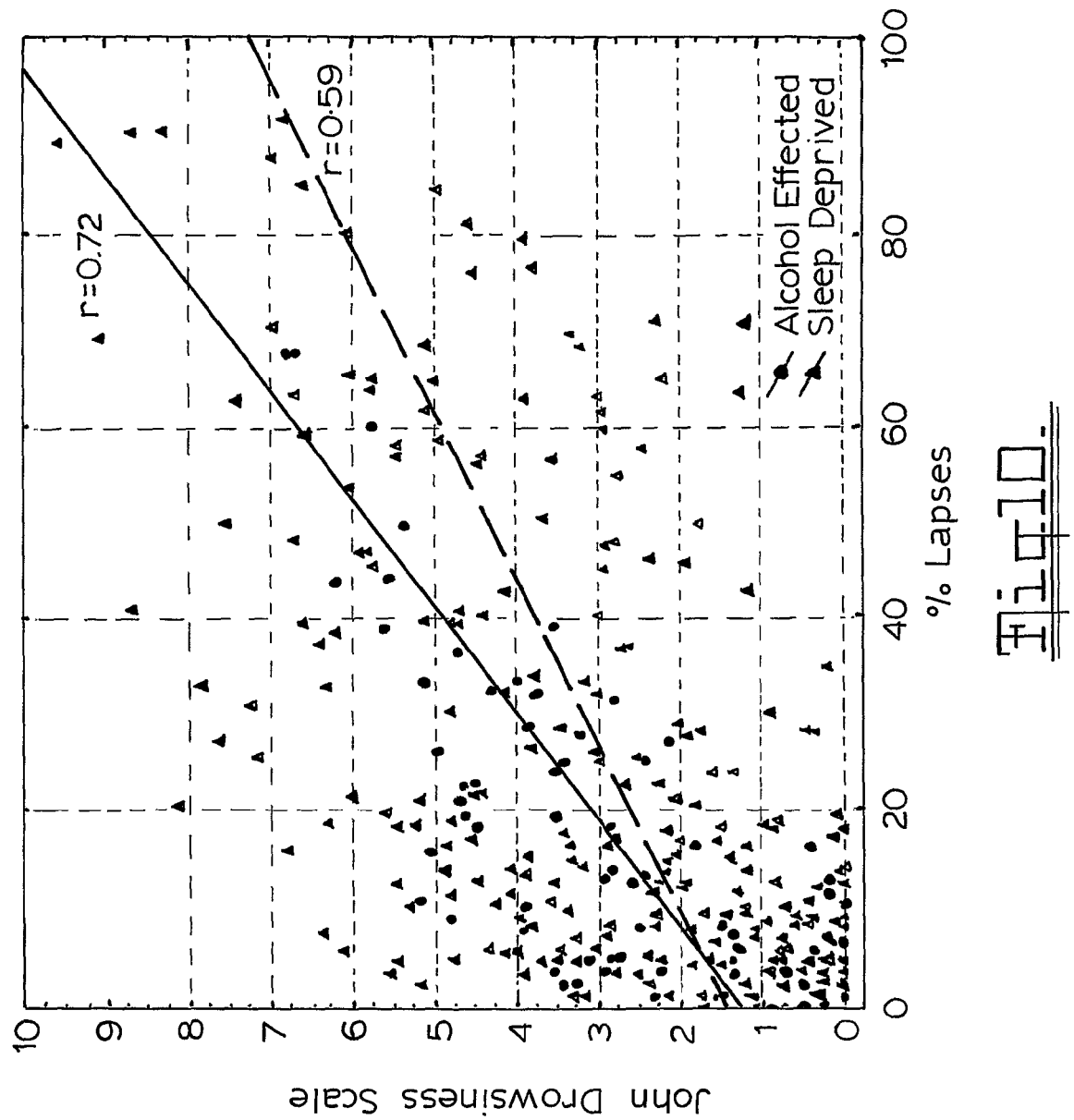

MEASURING ALERTNESS

This invention relates to monitoring alertness particularly in vehicle operators.

BACKGROUND TO THE INVENTION

The detection of drowsiness is of importance because drowsiness impairs the ability of operators of a wide range of equipment including motor vehicles, trains, aircraft and boats as well as industrial equipment. The problem of drowsy driving cannot be solved by educating drivers to take remedial action when feeling drowsy. The difficulty is that many people are unaware of their drowsiness at the time, even though they may be aware that they were drowsy after they rouse. This means one cannot predict when their level of drowsiness will next decrease to the point of danger because the drowsy state involves a loss of awareness of the present; an involuntary lapse of attention.

U.S. Pat. No. 5,745,038 discloses an eye monitor that examines reflected light from the eye to detect blinking behavior as an indicator of drowsiness.

U.S. Pat. No. 5,867,587 discloses a system which utilises digital images of the face and eyes of an operator, derives a parameter attributable to an eye blink and compares this to a threshold value of that parameter. A warning signal is given if the parameter falls below the threshold.

Patent specification WO 98/49028 also uses a video image as an eye gaze monitor to view a range of eye movements and analyse and compute a degree of alertness.

U.S. Pat. No. 6,091,334 discloses a system for analysing drowsiness which monitors head movement and gaze stability.

U.S. Pat. No. 6,102,870 uses eye tracker data such as fixations and saccades to infer mental states of the operator such as scanning, reading, searching, thinking and an intention to select. It is a system to enhance computer software responsiveness.

U.S. Pat. No. 6,097,295 discloses a system of image analysis based on eye pupil size.

U.S. Pat. No. 6,147,612 discloses a system of preventing sleep which detects eyelid movement and actuates an alarm when the eyelid movement is indicative of drowsiness.

U.S. Pat. No. 6,346,887 uses a video based eye tracking system which tracks eye activity and pupil diameter and position to produce a signal representing eye activity that can be used to estimate alertness.

WO 03/039358 disclosed an alertness monitor that used infra red light to measure the amplitude and velocity of eyelid and eye movements to derive a measure of alertness on a scale that can be related to the scale of blood alcohol levels. This monitor sought to provide a real time alertness monitor that can provide a calibrated measure of the operator's alertness.

It is an object of this invention to provide an improved alertness monitor of the type disclosed in WO 03/039358.

BRIEF DESCRIPTION OF THE INVENTION

To this end the present invention provides an alertness monitoring system which includes
a) means to measure eyelid movement
b) storage means to continuously record the measurements
c) a data processor to analyse eyelid movements to obtain measures of the amplitude and velocity of eyelid closing and opening averaging these over predetermined periods of time and measuring the deviation from a predetermined value for alert subjects
d) a display for showing the alertness measurement or
e) an alarm means triggered by the measurement reaching a predetermined value.

The amplitude to velocity ratio for eyelid opening and closing is used as the main measure of drowsiness onset. The ratio of the amplitude of to the maximum velocity (AVR) for both closing and opening during blinks increases with drowsiness and can be used to predict lapses in vigilance. This invention is partly predicated on the discovery that the AVR for eyelid closure and reopening are different for the same amplitude. Generally eyelids close more quickly than they reopen and the two velocities are only moderately correlated. The inventor has found that sleep deprivation increases AVR for both closing and reopening. Consequently the duration of these movements increase with drowsiness. The ratio it has been found that the ratio of opening velocity and amplitude is a major indicator of drowsiness. The ratio of the amplitude of opening to the maximum velocity (AVR) of opening has the dimension of time and is relatively constant with alert subjects but increases progressively with drowsiness and does not require calibration.

The values calculated for the purposes of comparison need to be averaged over a predetermined period of time. The eyelid parameters measured and the values selected for averaging can be determined by conducting trials and may be any suitable combination of parameters and averages. Preferably the velocity to amplitude ratios are calculated for each detected movement and then averaged over a predetermined interval. Other parameters such as duration of opening and closing may also be averaged and included in the final calculated value. It is also preferred to include eye movements such as saccades as additional parameters. The various parameters are preferably weighted in reaching the final calculation. This final calculation becomes an index of drowsiness with a low value indicating alertness and higher values indicating increasing levels of drowsiness. Eyelid and eye movement may be monitored using any suitable technology including video or digital camera technology to identify and measure the appropriate eye movements.

The storage means is used to store the signals sensed by the detector or the processed signals or the signals representing events used in the data processor. As explained in more detail below although absolute measurements of amplitude and velocity may be used it is preferred to use measures of relative amplitude and velocity to avoid the need for calibration. The average values may be calculated using any suitable statistical analysis of a plurality of readings and then using the mean or median value as explained in more detail below.

The display may be a graphical display on a screen, a numerical display, an auditory display or a printed report. The alarm system may be a flashing light or a noise and may include any of the alerts used with mobile phones such as ring tones, vibrations etc. Within vehicles the alarm may be a vibrating seat or tightening seat belt. The alarm merely needs to be sufficient to rouse the drowsy driver so that they may immediately stop.

The output data from the analyzer besides being used for the alarm may be kept as a record and/or transmitted to a control centre. Trucks are monitored for position and the alertness signals could easily be transmitted by wireless with the position information so that the central trucking station can analyse the data and monitor drivers online. The output signals as well as generating an alarm signal could also alter the operational state of the vehicle or machinery being used by the person being monitored. This could include braking the vehicle, disengaging power, or switching to a safe mode of operation.

DETAILED DESCRIPTION OF THE INVENTION

The drawings illustrate trial results of the invention in which

FIG. 10 illustrates the relationships between scores on the Johns Drowsiness Scale and the percentage of "lapses".

RECORDING FROM ONE OR BOTH EYES

The eye monitoring apparatus used in this invention is of the same kind as described in the inventor's earlier patent application WO 03/039358. WO 03/039358 described glasses with transducers (IR-LEDs and phototransistors) on both eyes. The reason for this was that binocular coordination changed with drowsiness which made it essential to record from both eyes. However, based on further research by the inventor, it appears that the measurement of binocular coordination becomes more inaccurate as drowsiness progresses. Thus where the measurement of binocular coordination is not required recordings from one eye are sufficient for all other parameters.

It is now preferred to use two infrared emitters and at least one photo transistor detector located on the lower frame member below one eye.

Currently, video camera methods for monitoring drowsiness have both practical and theoretical problems. Some of the latter may be overcome in the future if the frame rate of cameras can be increased to about 500 Hz, which may allow velocities and AVRs to be measured. At this time infra red emission and detection is the preferred technology.

Figure 1:
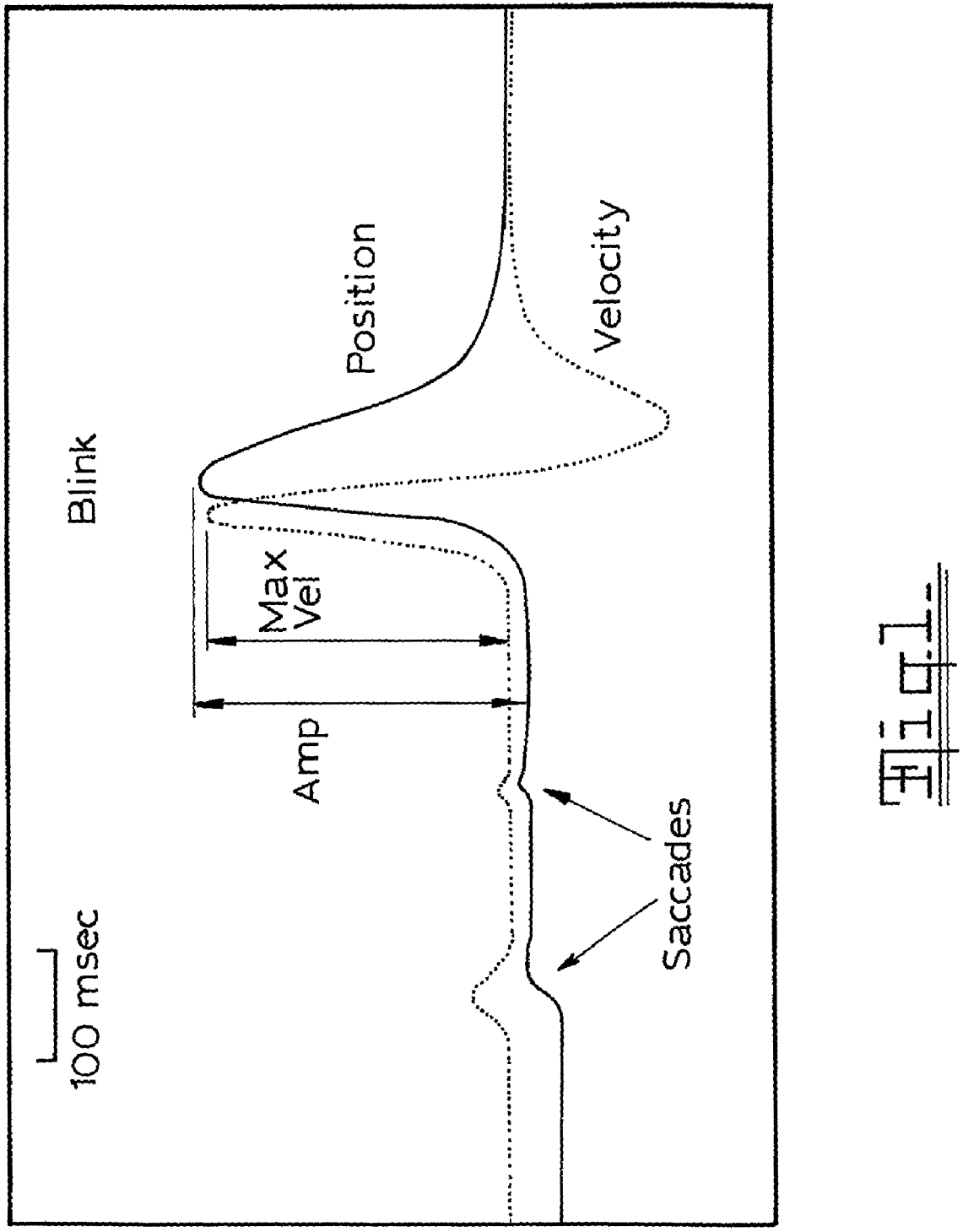
FIG. 1 is a recording using the method of this invention with an alert subject.

FIG. 1 shows the readings from using the present invention on an alert subject. On the vertical axis, position is in arbitrary units (A), and velocity is the change in A per 50 millisec.

Figure 2:
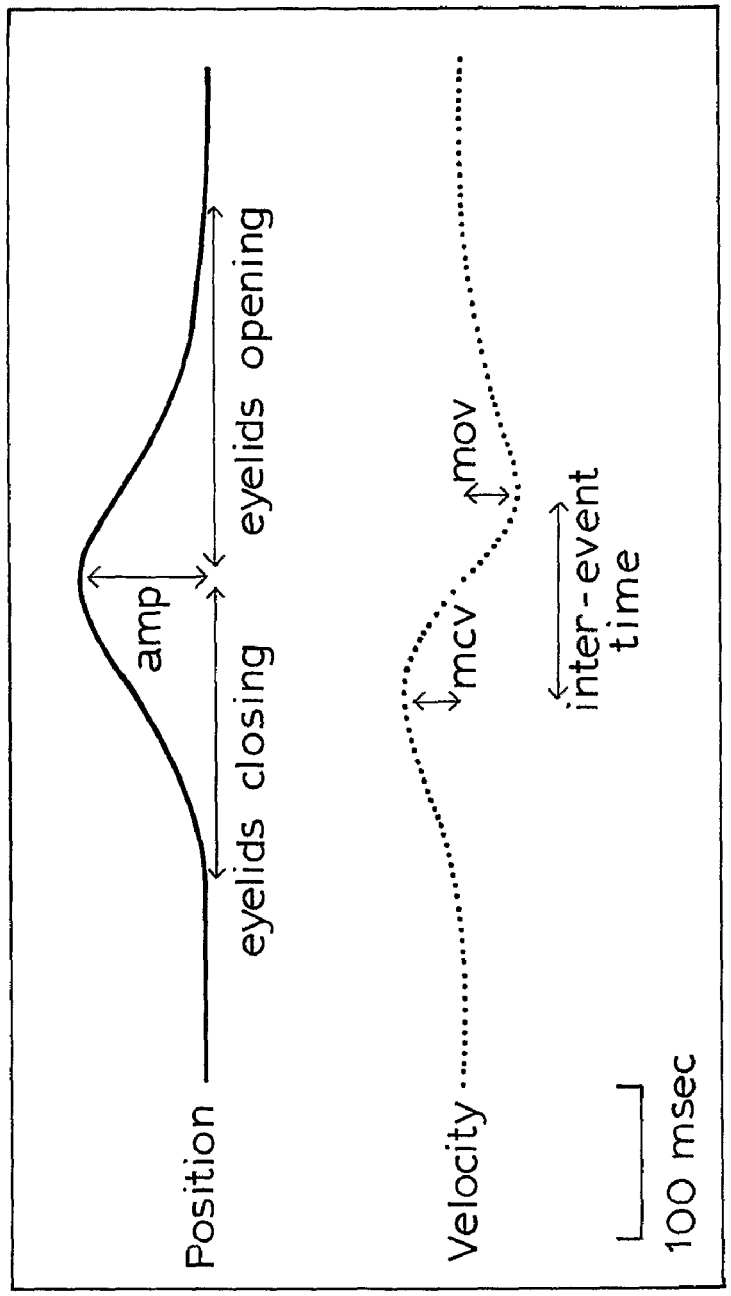
FIG. 2 is a recording of a blink using the method of this invention with a drowsy subject.
Figure 5:
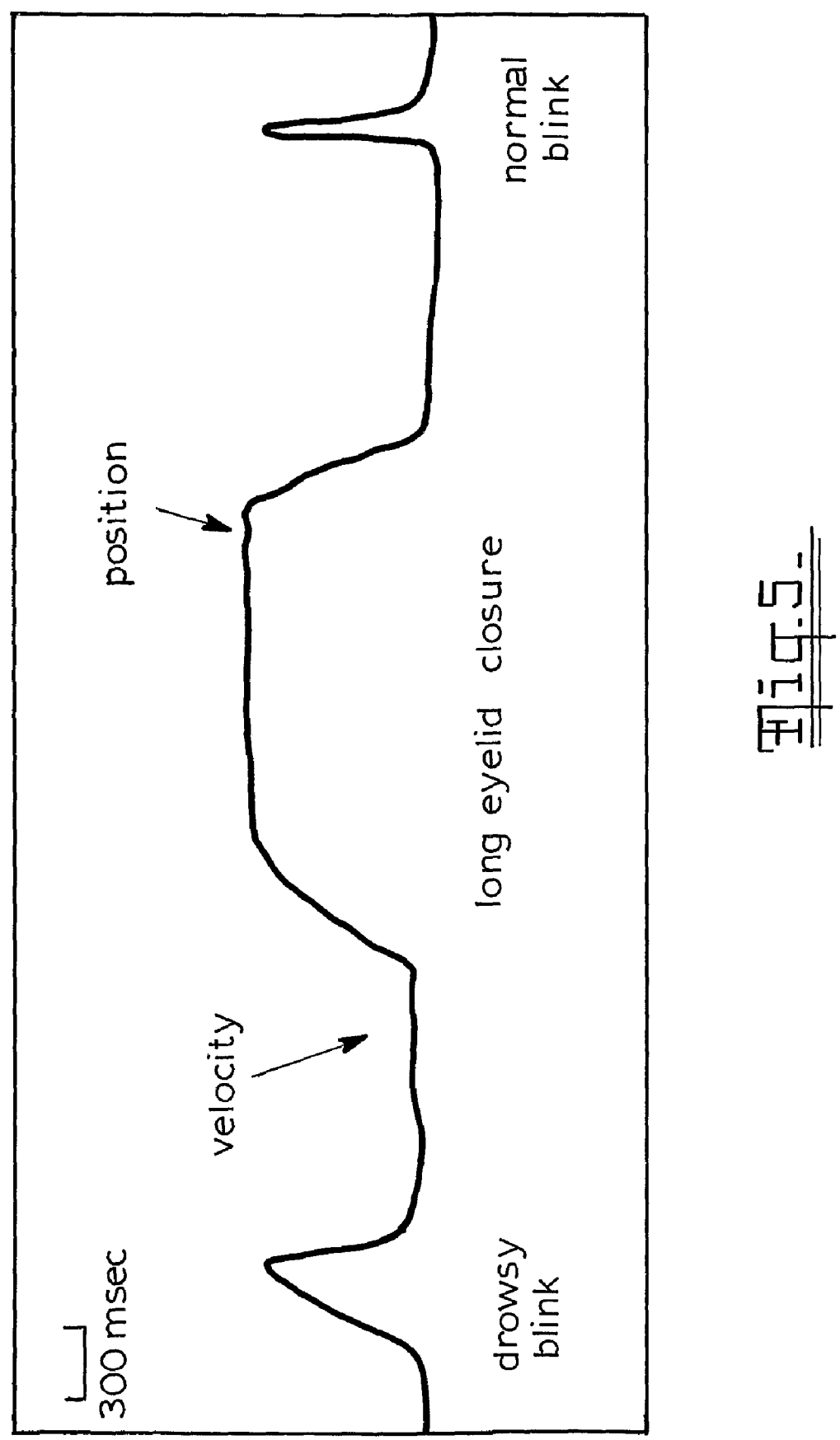
FIG. 5 illustrates blinks and long eyelid closure in a drowsy subject using the method of this invention.

FIG. 2 shows a blink in a drowsy subject from using the present invention
  amp=amplitude of blink
  mcv=maximum closing velocity of eyelid
  mov=maximum reopening velocity of eyelid
  inter-event time=a measure of blink duration
  velocity=change in position per 50 msec FIG. 5 shows blinks and long eyelid closure in a drowsy subject Amplitude-Velocity Ratios (AVRs)

In the alert state, it is known from WO 03/039358 that the amplitude of each blink or saccade is highly correlated with its maximum velocity. This invention is predicated in part on the discovery that velocity changes with drowsiness. The amplitude-velocity ratio (AVR) is an important measure of drowsiness. WO 03/039358 measured AVRs for blinks as well as for saccades. It is now preferred to rely on AVRs for blinks, excluding saccades and other movements. WO 03/039358 measured each AVR as the ratio of the amplitude of eyelid movement (the total change of position), measured in arbitrary units (A), divided by the maximum velocity of that movement, measured as the maximum change in A per 10 millisec. The inventor has now discovered that this accurately defined the relative velocity of most blinks and all saccades, but not of slower blinks that occur during drowsiness. It is now realized the velocity should be measured as the maximum change in A per 50 millisec. We distinguish this as AVR(50) instead of AVR(10).

WO 03/039358 was mainly concerned with AVR(10) in relation to eyelids closing during blinks. This invention is in part predicated on the discovery that closing and opening should be considered separately. This invention treats eyelids closing PAVR(50), and eyelids reopening NAVR(50), as separate variables. They are significantly different ($p<0.001$), but moderately correlated.

Figure 3:
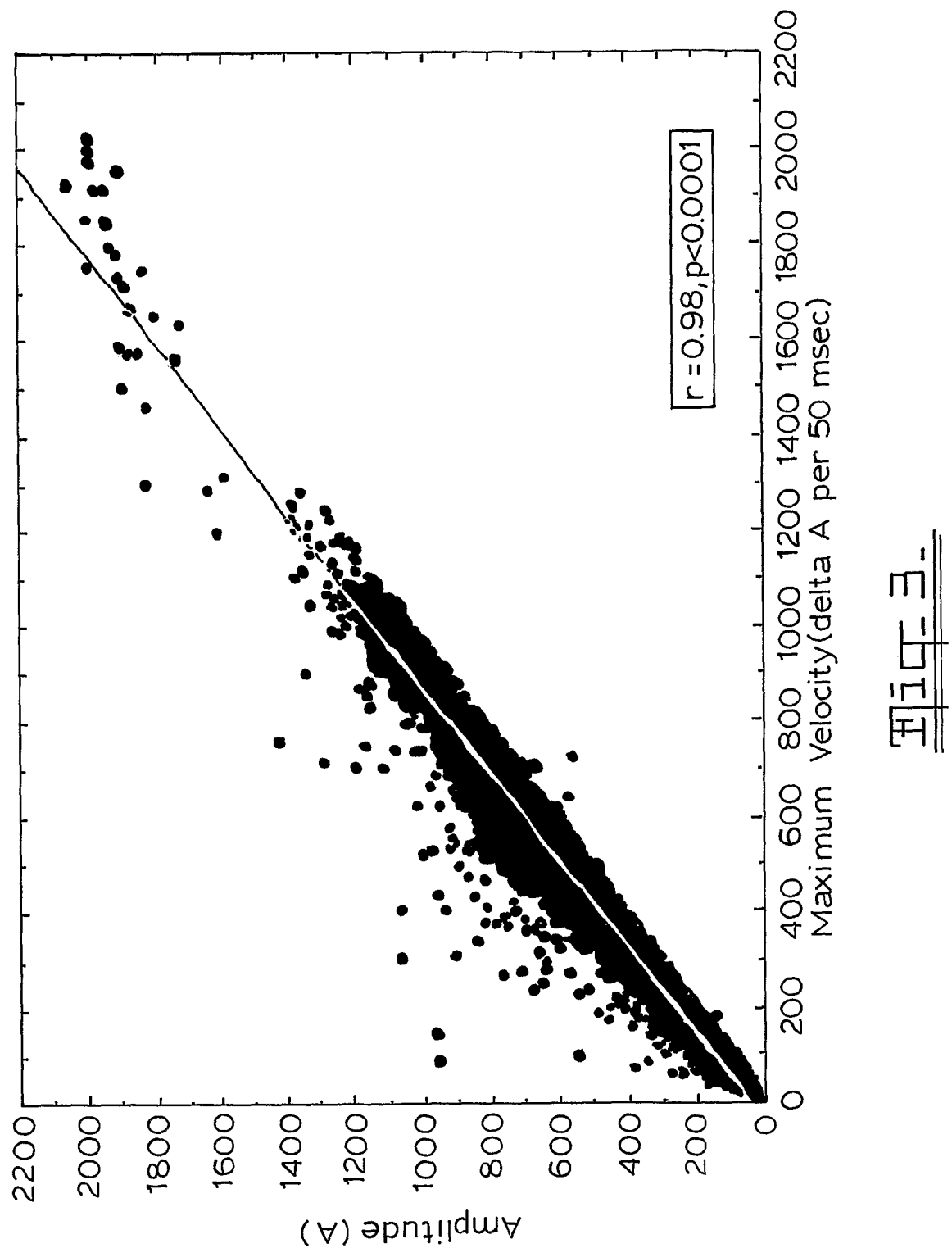
FIG. 3 illustrates amplitude versus maximum velocity for eyelid closure during blinks.

FIG. 3 illustrates amplitude versus maximum velocity for eyelid closure during blinks.

Figure 4:
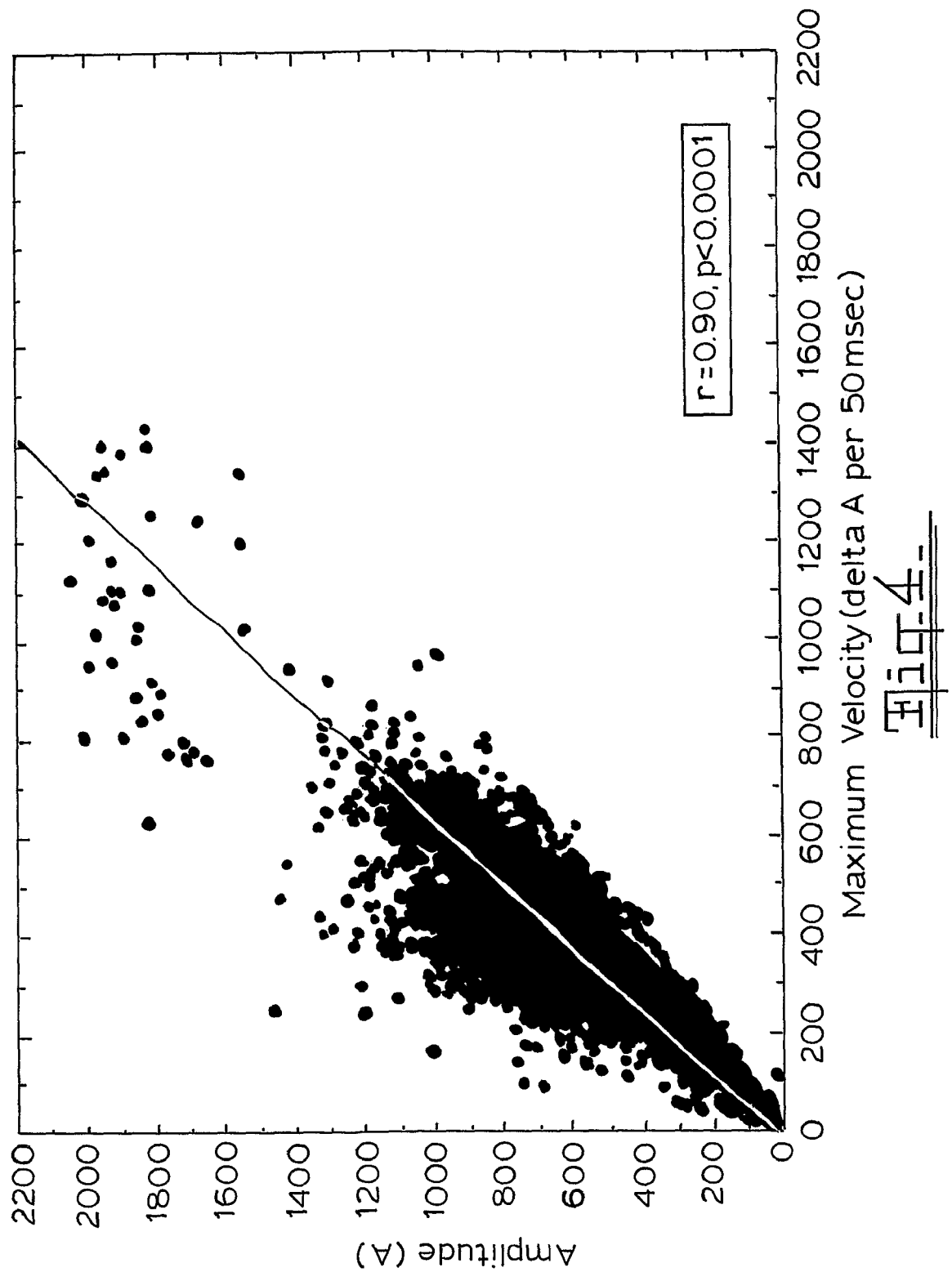
FIG. 4 illustrates amplitude versus maximum velocity for eyelid reopening during blinks.

FIG. 4 illustrates amplitude versus maximum velocity for eyelid reopening during blinks.

Duration of Eyelid Movements.

The duration of eyelids closing is measured as the interval between zero crossings in the velocity signal and is called the positive zero crossing interval (PZCI). The duration of eyelids reopening is measured separately as the negative zero crossing interval (NZCI). These PZCIs and subsequent NZCIs are only moderately correlated, even in the same subject ($r$=approx 0.5). These durations are highly correlated with but are not the same as, the respective AVRs for closing and opening.

The eyelids do not usually remain closed for more than 1-2 millisec during blinks in alert subjects, but with drowsiness this duration of closure increases markedly. This is measured as a separate variable (duration of eyelids closed). The total blink duration is measured as the sum of the duration of closing, duration of eyelids closed, and duration of reopening.

When the eyelids are reopening at the end of blinks they reach their maximum velocity when about half open, and then the remaining movement can be quite slow. This has always made it difficult to measure accurately the duration of that movement and hence the total duration of blinks. Other researchers have tried to overcome this by measuring the duration of blinks from the interval between the lids reaching half their respective amplitudes when closing and reopening.

This invention uses an alternative measure. It is the interval between the point of maximum velocity of closing and the subsequent maximum velocity of reopening, called the inter-event time. This must be distinguished from the interval between consecutive saccades, looking first to one side then the other, which occurs commonly in alert people. For blinks, the phase or direction of eyelid closing movement is always the same, downward (which we have arbitrarily called positive phase). This is followed by reopening which is always upward (negative phase). The negative inter-event time (NIET) is measured as the time between the maximum velocities of consecutive positive and negative movements, whatever their nature (this includes some consecutive saccades of the appropriate phase). The negative inter-event time gives a measure of the total duration of blinks which does not depend on the uncertainties of when the eyelid movements begin and end.

Relative Amplitude of Movements

It has proven to be much easier to distinguish blinks from other eye and eyelid movements in subjects when sitting still, doing a computer-based performance test, than when driving. The other kinds of eye movement when driving do not obey the same laws of amplitude and velocity used in measuring AVRs. Consequently, in this invention it is preferred to distinguish blinks from other movements. The method of this invention for doing this, is self-calibrating. Although normal blinks vary somewhat, they can be characterized by their duration and relatively large amplitude, in relation to other movements.

Reference ranges have been established for the "normal" duration of eyelids closing (PZCI) and for negative inter-event times (NIET) during blinks. When drowsy, many blinks exceed these "normal" ranges, but others still fall within them. The amplitude of these "normal" blinks are used as the reference for measuring the relative amplitude of all movements.

To calculate the relative amplitude of any movement, the "reference" amplitude for "normal" blinks for the particular subject at the time, must first be established, which can vary under different circumstances, such as the intensity of light at the time. The amplitude of each positive-phase movement that has a duration within the reference range for eyelid closure during "normal" blinks (eg PZCI=80-250 millisec) and which is followed by a negative-phase movement with an NIET within the reference range (eg 60-200 msec) is measured. These amplitudes are accumulated consecutively and, when twenty are accumulated, their $85^{th}$ percentile is calculated. This becomes the "reference" amplitude, which is otherwise uncalibrated, and which is continually updated during the recording, based on the twenty most recent measurements. The relative amplitude of all other movements, whether of positive or negative phase, is calculated as a percentage of that $85^{th}$ percentile.

The relative amplitude of most eye and eyelid movements other than blinks is <70%. That is particularly so for most horizontal and vertical saccades and for vestibulo-ocular movements that compensate for the subject's head movements when driving. Thus, almost all blinks can be distinguished by their relative amplitude being >70%. Once distinguished in this way, all blinks can be quantified, no matter how long their duration in the drowsy state.

Relative velocity is calculated as the change in units of relative amplitude per second.

A grimace is a forceful voluntary eyelid closure, usually seen only in the drowsy state when the eyes feel irritable. This can be distinguished from a normal blink by its high relative amplitude, typically >150%. No other method for monitoring eye and eyelid movements has distinguished grimaces before, so this is another unique feature of this invention.

Relative Position

It is important when the eyelids are not moving that they are distinguished as open or closed at the time. To do this the relative position of the eyelids must be known. This is done in this invention by recording the position every time a period of zero velocity begins and ends for events within the "normal" range of blinks, as defined above. All those position values are accumulated per minute. Then their $10^{th}$ and $90^{th}$ percentiles are calculated, as well as the difference between those percentiles. This is taken as the reference range of differences between relatively high (lids closed) and low (lids open) positions. Any particular position is then recorded as a percentage of that difference. For practical purposes the latter is assumed to be the "neutral" position, although in fact it is slightly above that. The relative position at any particular time is therefore a percentage of the difference between the $10^{th}$ and $90^{th}$ percentiles of previous movements.

The difference between relative amplitude and relative position, and the need for both in the analysis, may not be immediately obvious. The former is equivalent to the gain of the system, measured at times of maximum velocity, the latter to its DC offset, measured at times of zero velocity.

When there is direct sunlight on the phototransistors their amplifier output goes almost to zero. Recordings during that time are useless for determining drowsiness and must be removed from the analysis. This is done by simply removing all data points for (absolute) positions below (say) 200, whereas most other values are in the range 1000-2000.

The Johns Drowsiness Scale

Currently there is no generally applicable, calibrated scale for measuring a subject's level of drowsiness objectively at a particular time. There are methods for subjectively reporting feelings associated with drowsiness, such as the Stanford Sleepiness Scale (SSS) or the Karolinska Sleepiness Scale (KSS), that can measure relative changes within subjects, but they do not accurately reflect differences between subjects.

This invention provides the Johns Drowsiness Scale (JDS). The JDS is based on a weighted combination of variables describing the characteristics of eyelid and optionally eye movements that change with drowsiness and which are measured objectively by the device of this invention.

Table 1 shows variables and weightings in one embodiment of this invention.

TABLE 1

| Variable | B-weighting | Statistical Significance (p<) |
|---|---|---|
| $Log_n$ Standard deviation Inter-event time | 1.1575 | 0.00000 |
| Mean Positive AVR | −4.7422 | 0.00000 |
| Mean Negative AVR | 2.6295 | 0.00000 |
| $Log_n$ mean duration eyelids closed | 0.5116 | 0.00000 |
| $Log_n$ mean total duration of blinks | −1.9377 | 0.00002 |
| Standard deviation Positive AVR | 2.3916 | 0.0008 |
| Intercept (constant) | 7.9719 | 0.00000 |

This regression accounts for 62% of all variance between 60 sec periods for "alert" and "lapsing" data. (R=0.785: p<0.0000). These variables were selected statistically from about 20, involving both the mean and the standard deviation for most variables. The B-weightings were derived from comparisons between recordings made when subjects were alert (n=28) and able to respond within 2 second to at least 98% of visual stimuli presented to them in the Johns Test of Vigilance (JTV), and the same recordings made after 24-38 hr of sleep deprivation when the subjects were so drowsy (n=9) that they lapsed (failed to respond to the visual stimulus within 2 sec) at least 5% of the time in JTVs. It is assumed that a driver would not be fit to drive under the latter circumstances.

Figure 6:
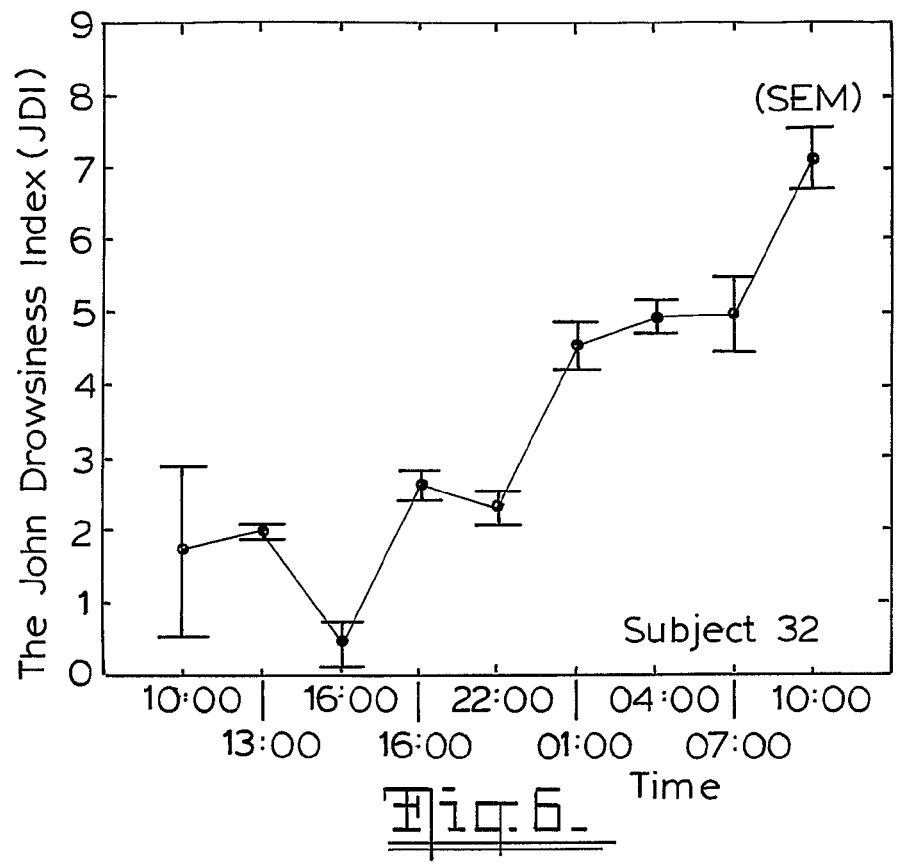
FIG. 6 illustrates the Drowsiness index of this invention for a subject kept awake over 24 hours.
Figure 7:
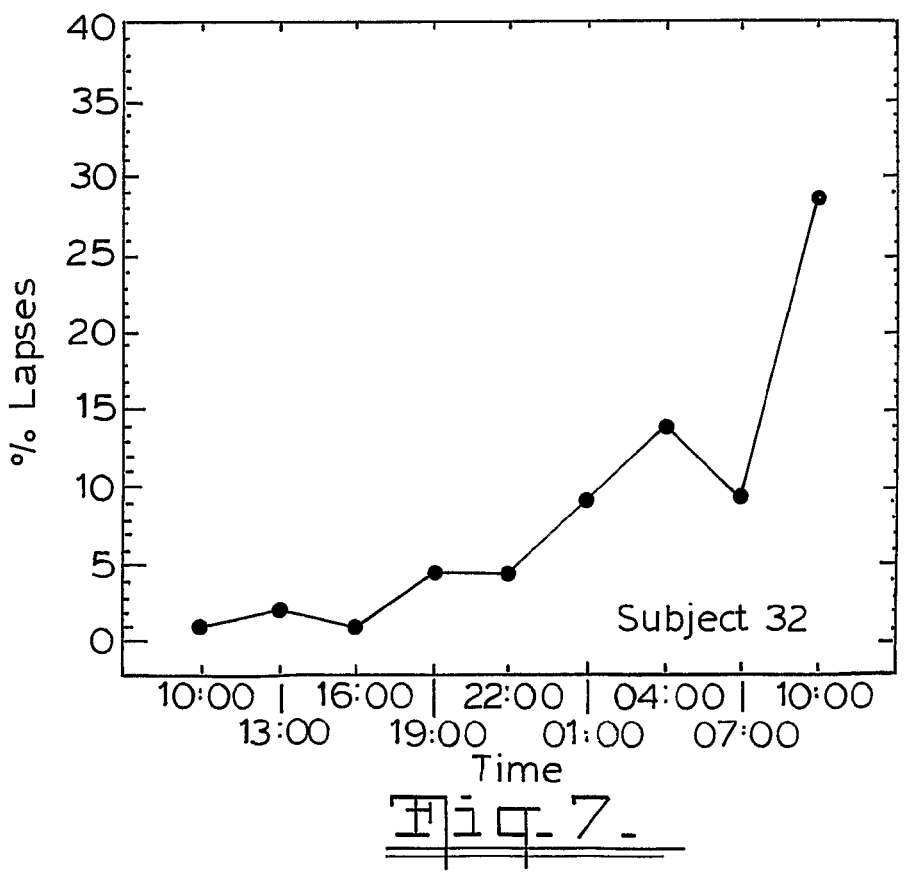
FIG. 7 illustrates the percentage of lapses using a test of vigilance over the same period.

FIGS. 6 and 7 illustrate the correlation between the drowsiness index and the lapse in vigilance in sleep deprived subjects.

The means and standard deviations for these variables were calculated for each minute of JTV recordings. Some variables that did not have a normal distribution were normalized by log (ln) transformation. There was more data for "alert" than for "lapsing" conditions because data were excluded for several subjects who were sleep deprived but did not lapse in JTVs, and who by this definition were not very drowsy at the time.

Statistical analysis was done first by stepwise multiple regression (forward and backward), using the selected variables to predict "alert" and "drowsy" conditions, coded as 1 and 8. The analysis was repeated with stepwise discriminant analysis and then with logistic regression analysis, each giving essentially the same results. The database was divided into two halves, and separate multiple regression analyses were performed on each half, which also gave very similar results. This supports the claim that the JDS is widely applicable across subjects. The variables being selected and their weightings may change slightly with an expanded database.

In other experiments, subjects were kept awake for 27 hr continuously, and they performed a 15-min JTV every 3 hours. The mean JDS increased progressively after midnight, as did the percentage of lapses in their performance of the JTV (p<0.001).

Calibration of the JDS may be made in terms of the decrement in performance on JTVs with increasing blood alcohol concentrations. This follows an earlier pilot study along the same lines which was able to demonstrate such a relationship. Similarly, the JDS may also be calibrated against the degree of impairment of driving skills in a driving simulator, comparing performance in the alert and sleep-deprived states.

In a second embodiment of the invention the algorithm is modified to take account of modified weightings and new variables such as the mean duration of ocular quiescence (DOQ) per minute. This is the mean of the intervals between consecutive eye and eyelid movements of any kind, including saccades, blinks, vestibulo-ocular movements, etc. Relatively long periods of ocular quiescence are typical of the drowsy state for many subjects. Another new variable is the percentage of saccades that have an AVR above a given threshold (% high AVR saccades) This percentage increases with drowsiness.

Table 2 shows variables and weightings in this second embodiment of this invention.

TABLE 2

| Variable | B-weight | Statistical Significance (p<). |
|---|---|---|
| Ln mean negative zero crossing interval | 2.66 | 0.00001 |
| Ln standard deviation inter event time | 0.99 | 0.00001 |
| Ln mean duration of eyelid closure | 0.07 | 0.003 |
| Ln standard deviation negative AVR | 0.22 | 0.00001 |
| Percentage of saccades with high AVR | 0.01 | 0.001 |
| Ln mean duration of ocular quiescence | −1.49 | 0.00001 |
| Constant | 13.83 | 0.00001 |

The results of many experiments by the applicant have shown the JDS can be calibrated in terms of a "critical level" of drowsiness that can be applied generally, with greater accuracy and sensitivity, by comparing JDS values with the results of psycho-physiological performance tests.

JDS values were measured each minute during reaction-time tests (The Johns Test of Vigilance or JTV) in many subjects who were drowsy because they had been sleep-deprived to some extent, or had drunk different amounts of alcohol, or had some other cause of their drowsiness. Different levels of drowsiness, as reflected in JDS scores, were then described in terms of levels of impairment in the performance of those standardized tests, such as slowing of visual reaction-times and how often the subject failed to respond at all to a meaningful visual stimulus. These results indicate that when a driver's drowsiness reaches a "critical" level, equal to or greater than 5.0 on the JDS, he/she is no longer fit to drive. This JDS score is associated with a reasonably high chance of not responding to a meaningful visual stimulus presented within the visual field. For safe driving, the ability to respond to clear and relevant visual stimuli, such as a stop-light on the vehicle ahead or a bend in the road, is paramount.

Figure 8:
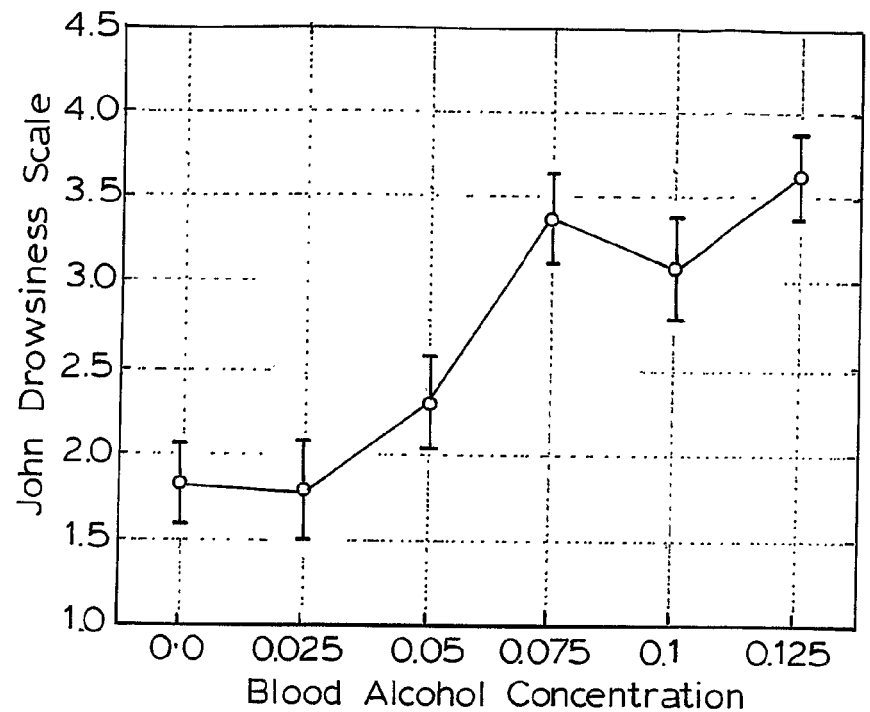
FIG. 8 illustrates the relationship between the Johns Drowsiness Scale (JDS) and blood alcohol concentration.

FIG. 8 shows the relationship between the Johns Drowsiness Scale (JDS) and blood alcohol concentration (g %) in 19 subjects. [Error bars are 95% confidence intervals. ANOVA p<0.0001]

There was a statistically significant relationship between JDS scores, measured during a standardized test (10-min JTV) in 19 volunteer subjects, and their BAC measured by breathalyzer during an evening when they drank progressively more alcohol between 6 μm and midnight.

In the JTV the subject is asked to push a button (held in his/her dominant hand) as quickly as possible after seeing a change of shapes on a computer screen. The changes occur at random intervals between 5 and 15 sec Three circles on the screen change to either squares or diamonds for 400 msec. This gives alert subjects ample time to see that change, and they seldom fail to respond when alert. Their reaction-times (RT), each measured with an accuracy of 2 msec, are usually less than 500 msec.

When drowsy, their responses change in several ways.
1. They take longer to respond to each stimulus (longer reaction-times)
2. They fail more often to respond at all, ie they make more errors of omission.

These changes with drowsiness are assessed by calculating a mean RT for each JTV test, and the percentage of times that the subject fails to respond within particular time limits (0.5, 1.0 or 2.0 sec) is also calculated.

Figure 9:
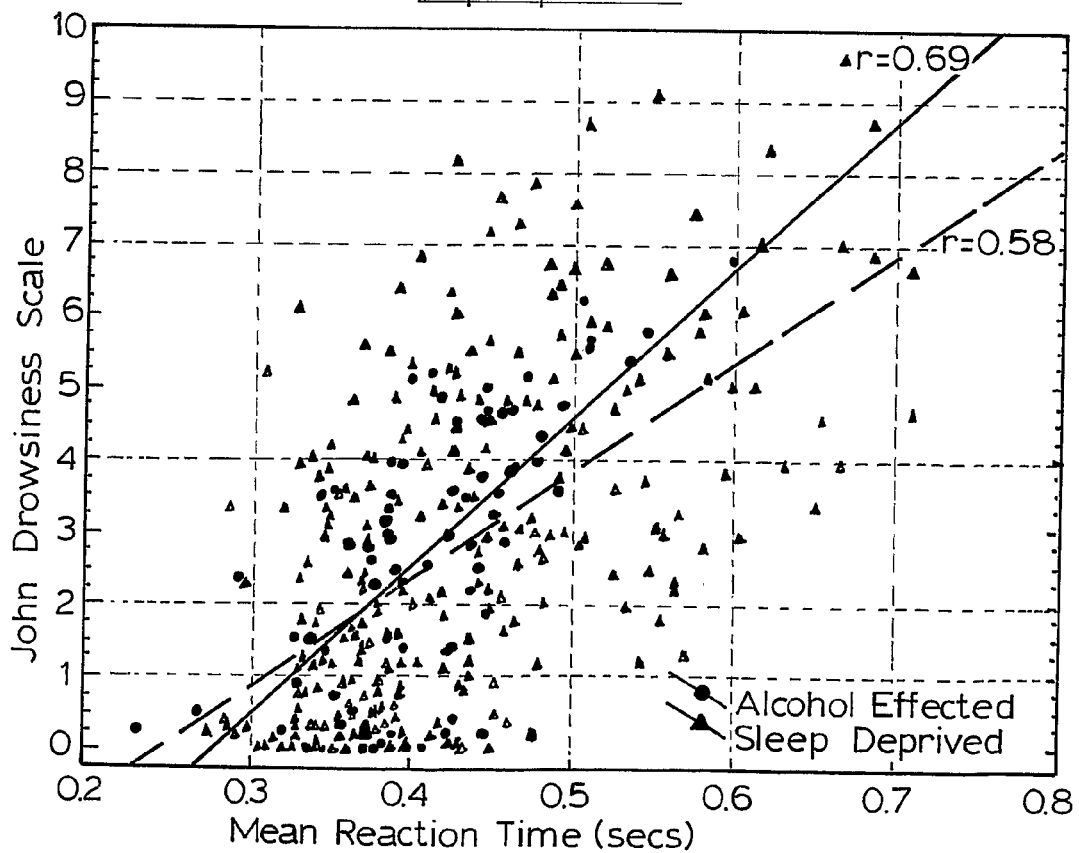
FIG. 9 illustrates the relationships between scores on the Johns Drowsiness Scale and mean reaction-times.

The JDS scores and RTs during JTVs in many subjects at different levels of drowsiness because of sleep deprivation, have been measured with up to 40 hours of continuous wakefulness. The JDS scores and RTs in the 19 subjects with different levels of blood alcohol, have also been measured as shown in FIG. 8. The combined results for 70 subjects who performed a total of 221 JTVs done by 51 sleep-deprived subjects (red triangles and dashed line) and 19 alcohol-effected subjects (blue circles and continuous line) are shown in FIG. 9.

There is a highly significant linear relationship between JDS and RT in each group of subjects, and their regressions are similar. Higher JDS scores are associated with slower responses to the visual stimulus in the JTV (higher RTs). This is true regardless of the cause of drowsiness A JDS of 5 is associated with mean RTs in excess of 500 msec. While there is no generally accepted critical value for such RTs, these are slow responses which presumably contribute to an increased crash risk.

The JDS is an objective physiological measure of ocular function and the RT is a measure of behaviour that is clearly related to the task of driving. In psychophysiological research it is not common to have correlations between such variables at 0.6-0.7 in a database of this size.

FIG. 10 shows the relationships between scores on the Johns Drowsiness Scale and the percentage of "lapses" in 221 JTVs performed by 51 sleep-deprived subjects (red triangles and dashed line) and 19 alcohol effected subjects (blue circles and continuous line).

FIG. 10 shows similar relationships, in the same two groups of subjects as in FIG. 9, between JDS scores and the percentage of "lapses" in the JTV, when there was either no response or a delayed response with RT>500 msec. This is particularly relevant to the driving situation where failure to respond, or to respond quickly enough to a clear visual stimulus may be of critical importance These are also highly significant relationships which provide further evidence for the validity of the JDS. A JDS of 5 is associated with a high chance of lapsing in the performance test, and presumably also while driving.

From the above description it can be seen that the present invention provides a unique measure of drowsiness and a reliable predictor of a person's capacity to operate machinery or vehicles where alertness is required.

Those skilled in the art will realize that the benefits of this invention can be achieved by embodiments of the apparatus and methodology other than those described without departing from the core teachings of this invention.

The invention claimed is:

1. A computerized method of measuring drowsiness of a subject which includes the steps of:
   a) continuously monitoring eyelid movement of at least one eye of a subject;
   b) measuring amplitude of eyelid movement;
   c) measuring the maximum velocity for eyelid opening and closing, individually;
   d) using an algorithm to obtain separate values for the amplitude to velocity ratio for eyelid opening and closing, respectively;
   e) separately averaging the values for the amplitude to velocity ratios for opening and closing, respectively, over predetermined intervals;
   f) recording the separate averaged values for each interval, weighting the separate values differently and adding them to give a drowsiness measure that is compared to a scale of drowsiness based on data collected from alert and drowsy subjects.

2. A method as claimed in claim 1 in which the drowsiness measure also includes the mean of the intervals between consecutive eye and eyelid movements of any kind.

3. A method as claimed in claim 1 in which the drowsiness measure also includes the percentage of saccades with a high amplitude to velocity ratio.

4. A method as claimed in claim 1 in which the average duration of eyelid blinks and eyelid closures within a predetermined interval are included in the measure of drowsiness.

5. A computerized method of measuring drowsiness of a subject which includes the steps of:
   a) continuously monitoring eyelid movement of at least one eye of a subject;
   b) measuring amplitude of eyelid movement;
   c) measuring the maximum velocity for eyelid opening and closing, individually;
   d) using an algorithm to obtain separate values for the amplitude to velocity ratio for eyelid opening and closing, respectively;
   e) separately averaging the values for the amplitude to velocity ratios for opening and closing, respectively, over predetermined intervals;
   f) recording the separate averaged values for each interval, weighting the separate values differently and adding them to give a drowsiness measure that is compared to a scale of drowsiness based on data collected from alert and drowsy subjects.

6. A non-transitory medium storing instructions adapted to be executed by a processor to calculate a measure of alertness, the instructions comprising:
   a) continuously monitoring eyelid movement of at least one eye of a subject;
   b) measuring amplitude of eyelid movement;
   c) measuring the maximum velocity for eyelid opening and closing, individually;
   d) using an algorithm to obtain separate values for the amplitude to velocity ratio for eyelid opening and closing, respectively;
   e) separately averaging the values for the amplitude to velocity ratios for opening and closing, respectively, over predetermined intervals;
   f) recording the separate averaged values for each interval, weighting the separate values differently and adding them to give a drowsiness measure that is compared to a scale of drowsiness based on data collected from alert and drowsy subjects.

* * * * *